United States Patent [19]
Bryan et al.

[11] Patent Number: 5,994,508
[45] Date of Patent: *Nov. 30, 1999

[54] ISOFLAVONE RICH PROTEIN ISOLATE AND PROCESS FOR PRODUCING

[75] Inventors: Barbara A. Bryan, University City; Balagtas F. Guevara, Sunset Hills, both of Mo.

[73] Assignee: Protein Technologies International, Inc., St. Louis, Mo.

[*] Notice: This patent is subject to a terminal disclaimer.

[21] Appl. No.: 09/059,513

[22] Filed: Apr. 13, 1998

[51] Int. Cl.$^6$ .................................. A23J 1/14; A23L 2/38
[52] U.S. Cl. ..................... 530/378; 530/370; 530/350; 530/412; 530/418; 530/420; 530/427; 426/433; 426/434; 426/598
[58] Field of Search ..................... 530/378, 370, 530/350, 412, 418, 420, 427; 426/433, 434, 598

[56] References Cited

U.S. PATENT DOCUMENTS

| | | | |
|---|---|---|---|
| 5,320,949 | 6/1994 | Shen | 435/68.1 |
| 5,637,561 | 6/1997 | Shen et al. | 514/2 |
| 5,637,562 | 6/1997 | Shen et al. | 514/2 |
| 5,702,752 | 12/1997 | Gugger et al. | 426/634 |
| 5,726,034 | 3/1998 | Bryan et al. | 435/68.1 |
| 5,827,682 | 10/1998 | Bryan et al. | 435/68.1 |

FOREIGN PATENT DOCUMENTS

| | | |
|---|---|---|
| 0647408 | 12/1995 | European Pat. Off. . |
| WO 97/37547 | 10/1997 | WIPO . |

*Primary Examiner*—Michael P. Woodward
*Assistant Examiner*—Abdel A. Mohamed
*Attorney, Agent, or Firm*—Richard B. Taylor

[57] ABSTRACT

A process for providing an isoflavone rich protein isolate is provided, along with the isoflavone rich protein isolate produced thereby. A vegetable material containing protein and at least one isoflavone compound is extracted with an aqueous extractant having a neutral pH. The protein and isoflavones are extracted into the extractant, and the extractant containing the protein and isoflavones is separated from insoluble vegetable materials to form a protein extract. The pH of the protein extract is adjusted to about the isoelectric point of the protein to precipitate the protein. The extract containing the precipitated protein is cooled to a temperature of from about 40° F. to about 80° F., and then the protein is separated from the extract. The cool separation temperatures unexpectedly significantly increase the concentration of isoflavones recovered in the separated protein, while the neutral extract pH inhibits loss of protein normally observed at cool or cold separation temperatures.

15 Claims, No Drawings

ISOFLAVONE RICH PROTEIN ISOLATE AND PROCESS FOR PRODUCING

BACKGROUND OF THE INVENTION

The present invention relates to an isoflavone enriched vegetable protein isolate and a process for producing the same.

Isoflavones occur in a variety of leguminous plants and oilseeds, including vegetable protein materials such as soybeans. These compounds, for purposes of the present invention, include daidzin, 6"-OAc daidzin, 6"-OMal daidzin, daidzein, genistin, 6"-OAc genistin, 6"-OMal genistin, genistein, glycitin, 6"-OMal glycitin, glycitein, biochanin A, and formononetin. As used herein, "Mal" represents "malonyl" and "Ac" represents "acetyl". The structures of these isoflavones are shown in Formulas 1 and 2 below.

Formula 1

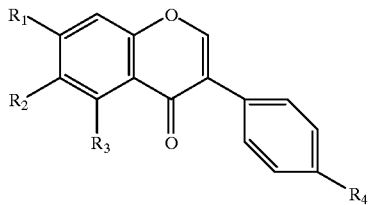

| Compound | $R_1$ | $R_2$ | $R_3$ | $R_4$ |
|---|---|---|---|---|
| Genistein | OH | H | OH | OH |
| Daidzein | OH | H | H | OH |
| Glycitein | OH | $OCH_3$ | H | OH |
| Biochanin A | OH | H | OH | $OCH_3$ |
| Formononetin | OH | H | H | $OCH_3$ |

Formula 2

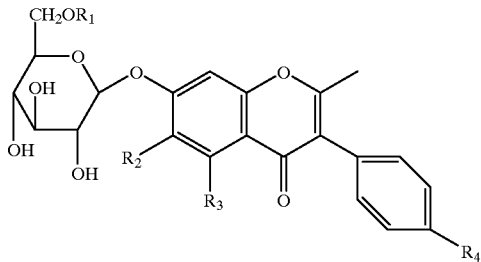

| Compound | $R_1$ | $R_2$ | $R_3$ | $R_4$ |
|---|---|---|---|---|
| Genistin | H | H | OH | OH |
| 6"-OMal genistin | $COCH_2CO_2H$ | H | OH | OH |
| 6"-OAc genistin | $COCH_3$ | H | OH | OH |
| Daidzin | H | H | H | OH |
| 6"-OMal daidzin | $COCH_2CO_2H$ | H | H | OH |
| 6"-OAc daidzin | $COCH_3$ | H | H | OH |
| Glycitin | H | $OCH_3$ | H | OH |
| 6"-OMal glycitin | $COCH_3$ | $OCH_3$ | H | OH |

It has recently been recognized that the isoflavones contained in vegetable proteins such as soybeans may inhibit the growth of human cancer cells, such as breast cancer cells and prostate cancer cells, as described in the following articles: "Genistein Inhibition of the Growth of Human Breast Cancer Cells: Independence from Estrogen Receptors and the Multi-Drug Resistance Gene" by Peterson and Barnes, *Biochemical and Biophysical Research Communications*, Vol. 179, No.1 p. 661–667, Aug. 30, 1991; Genistein and Biochanin A Inhibit the Growth of Human Prostate Cancer Cells but not Epidermal Growth Factor Receptor Tyrosine Autophosphorylation" by Peterson and Barnes, *The Prostate* 22: 335–345 (1993); and "Soybeans Inhibit Mammary Tumors in Models of Breast Cancer" by Barnes et al. *Mutagens and Carcinogens in the Diet* p. 239–253 (1990). These isoflavones also have been found to reduce cardiovascular risk factors, for example by reducing the levels of atherosclerosis inducing lipoproteins and low density cholesterol and by increasing endothelial dependent vasodilation response.

Typically these isoflavone compounds have been associated with an inherent, bitter flavor in vegetable protein materials such as soybeans. In the commercial production of such protein materials, such as protein isolates and protein concentrates, the focus has been to remove these isoflavone compounds.

In a typical conventional process for the production of a vegetable protein isolate, e.g. a soy protein isolate, a vegetable material containing protein is extracted with an aqueous alkaline extractant, typically having a pH of from about 8 to about 11, to extract protein from insoluble vegetable matter. The extractant preferably is relatively alkaline, usually having a pH of from about 9 to 10, since vegetable proteins are very soluble in extractants of higher alkalinity, leading to extraction of most of the protein from the vegetable material. The extractant containing the protein is separated from insoluble vegetable materials to provide a protein extract.

The protein isolate is then recovered from the protein extract. A protein material is precipitated from the extract by adjusting the pH of the extract to about the isoelectric point of the protein with a suitable acid. The precipitated protein material is then separated from the extract. Typically the protein material is separated from the extract at a temperature of from about 120° F. to 150° F. since the precipitated protein packs densely at these temperatures, enhancing the yield of the recovered protein material. Separation temperatures below 90° F. are avoided since the protein becomes fluffy at such temperatures, reducing the yield and commercial usefulness of the recovered protein material. After the protein material is separated from the extract, the protein material is extensively washed to remove residual carbohydrates, isoflavones, ash, and other non-protein materials.

When the vegetable material contains isoflavones, in addition to protein, the isoflavones are solubilized by the aqueous extractant along with the protein. Much of the isoflavones remain solublized in the extract following separation of the precipitated protein material from the extract. After separation of the precipitated protein material from the extract, the extract and isoflavones solubilized therein are usually discarded. Residual isoflavones left in the separated protein material are usually removed by exhaustive washing of the protein material to ensure that the taste associated with the isoflavones is not present in the protein material.

It is desirable, however, to provide an isoflavone rich protein material, and a process for producing the same, which is suitable for administration in a diet. Such an isoflavone rich protein material can be used to provide the nutritional benefits of the protein and the health benefits of the isoflavones when administered in a diet.

SUMMARY OF THE INVENTION

The present invention is a process for producing an isoflavone rich protein material, and the resulting isoflavone rich protein material. A vegetable material containing protein and isoflavones is extracted with an aqueous extractant having a substantially neutral pH and the extractant is separated from insoluble vegetable materials to produce an extract containing the isoflavones and protein. The pH of the extract is adjusted to about the isoelectric point of the protein to precipitate a protein material containing isoflavones. The protein material is separated from the extract at a temperature of about 30° F. to about 90° F., and washing of the separated protein material is avoided to produce the isoflavone rich protein material.

In another aspect the present invention is a process similar to that described above, except that the separated protein material is washed with water. In a preferred embodiment, the separated protein material is washed with water in an amount by weight which is less than about four times the weight of the initial vegetable material, and more preferably, less than about two times the weight of the initial vegetable material. In another preferred embodiment, the water used to wash the separated protein material has a temperature of about 30° F. to about 90° F.

In a preferred embodiment, the isoflavones in the protein material prepared according to the present invention include at least one of the following: daidzin, 6"-OMal daidzin, 6"-OAc daidzin, daidzein, genistin, 6"-OMal genistin, 6"-OAc genistin, genistein, glycitin, 6"-OMal glycitin, glycitein, biochanin A, formononetin, or a mixture thereof.

The isoflavone content of a protein material separated from a vegetable material containing protein and isoflavones using a process of the present invention is significantly higher than that of a protein material separated from such a vegetable material using a conventional protein separation process. First, either avoiding washing the separated protein material with water or using limited amounts of water to wash the separated protein material increases the amount of isoflavones retained in the protein material relative to a conventional process in which the separated protein material is extensively washed. Second, separation of the precipitated protein material from the extract at cool or cold temperatures unexpectedly significantly increases the amount of isoflavones trapped in the separated protein material. The inventors of the present invention have found that cool or cold separation of the protein material at temperatures below 90° F. greatly increases the amount of the desired isoflavones recovered in the protein material.

The separation of the precipitated protein material at cool or cold temperatures has been avoided in conventional protein separation processes to preclude the formation of a fluffy protein. The inventors have also discovered that formation of a fluffy protein at cool or cold separation temperatures below 90° F. can be avoided by extracting the intial vegetable material with a substantially neutral aqueous extractant, rather than a moderately strong or strong aqueous alkaline solution. The precipitated protein material formed from a substantially neutral aqueous extractant unexpectedly packs together in a dense mass even at cool or cold temperatures below 90° F., enabling the protein material to be recovered in a yield comparable to the yield of a protein material recovered in a conventional process, where the recovered protein material is rich in isoflavones as a result of the low temperature separation process. Therefore, utilizing a neutral aqueous extractant permits the isoflavone content of the protein material to be increased by separating the protein from the extract at cool or cold temperatures without a loss of protein yield typically caused by fluffy protein formation at temperatures below 90° F.

DESCRIPTION OF THE PREFERRED EMBODIMENTS

Although the present invention will be described with respect to soybean materials, and the process is particularly suited for production of an isoflavone rich protein isolate from soybean materials, nevertheless, the present process is generally applicable to the production of protein isolates from a variety of vegetable protein sources which contain isoflavones. Other vegetable protein sources which contain isoflavones which may be used in the process of the present invention include, but are not limited to, one or more of the following plant materials: chick pea, ground pea, marama bean, sword bean, jack bean, seaside sword bean, caraobean, cluster bean, hyacinth bean, grass pea, garden pea, djenko bean, goa bean, yam bean, broad bean, earth pea, lentil, jumping bean, velvet bean, African locust bean, and derivatives of such plant materials.

A soybean starting material for the process of the present invention is a soybean material containing soy protein and isoflavones such as soy flakes, soy meal, and soy flour. The isoflavone compounds contained in the soybean starting material typically include genistin, 6"-OMal genistin, 6"-OAc genistin, genistein, daidzin, 6"-OMal daidzin, 6"-OAc daidzin, daidzein, glycitin, 6"-OMal glycitin, and glycitein, shown in Formulas 1 and 2 above. The soybean starting material may be modified to adjust the isoflavone content in the starting material, for example by conversion of the isoflavone conjugates and isoflavone glucosides of Formula 2 to the more biologically active aglucone isoflavones of Formula 1 by enzymatic conversion, prior to use of the starting material in the process of the present invention.

The preferred starting material for the process of the invention is soy flakes from which the oil has been removed by solvent or mechanical extraction, and which may be produced from soybeans according to conventional processes. The process of the invention will be described with respect to a soy flake starting material, although other soy protein and vegetable protein containing starting materials may be used in place of the described soy flakes.

Initially, the flakes are extracted with an aqueous extractant having a substantially neutral pH to extract the protein and isoflavones from the flakes. As used herein, a substantially neutral pH is defined as the pH range from about pH 6 to about pH 8. Use of a substantially neutral pH extractant is required to maximize the amount of protein material recovered from the extract during separation of the protein material from the extract at cool or cold temperatures by inhibiting the formation of a fluffy protein precipitate. Most preferably the pH of the aqueous extractant is from about pH 6.5 to about pH 7.5. Typical alkaline or acidic reagents may be employed, if needed, to adjust the pH of the aqueuous extractant to a desired pH including sodium hydroxide, potassium hydroxide, calcium hydroxide, hydrochloric acid, sulfuric acid, acetic acid, and phosphoric acid.

The desired isoflavone compounds are solubilized in the aqueous extract along with the protein, and, in order to maximize recovery of these compounds in the aqueous extract, the weight ratio of flakes to aqueous extract is preferably controlled to specific levels in order to solubilize as much of the isoflavones and protein as possible. Extraction of the proteins and isoflavones can be carried out in a variety of ways including countercurrent extraction of the flakes, preferably at a weight ratio of extractant to flakes of about 5:1 to about 12:1 in which the initial extract is used to reextract the flakes and provide an aqueous extract of protein and isoflavones. Alternatively, a two-step extraction process can be used, preferably in which the weight ratio of extractant to flakes in an initial step is about 8:1 and a second extraction of the flakes with fresh extractant is effected at a weight ratio of extractant to flakes of about 3:1 to about 6:1 so that the combined weight ratio of the extractant to flakes in both steps does not exceed a total weight ratio of extractant to flakes of about 1 1:1 to about 14:1.

Although not critical, the extraction may be carried out at temperatures up to about 120° F., preferably at about 90° F., for a period of time of about 5 minutes to about 60 minutes, preferably for about 15 minutes.

The aqueous extractant containing the protein material and isoflavones is then separated from the insoluble vegetable materials. The extract may be separated from the insoluble vegetable materials by conventional liquid/solid separation processes such as filtration or centrifugation. In a preferred embodiment, the protein/isoflavone extract is separated from the insoluble materials by centrifuge, and the extract is collected as the supernatant.

The pH of the resulting aqueous protein extract containing isoflavones is adjusted to about the isoelectric point of the protein with an edible acid to precipitate an isoflavone containing protein material to enable the protein material to be separated from other water soluble materials extracted from the vegetable material such as carbohydrates and ash. The isoelectric point for soy protein is generally between about pH 4.0 to about 5.0, and more specifically between a pH of about 4.4 to about 4.6. The edible acid added to adjust the pH of the extract to about the isoelectric point of the protein may be any suitable edible acid such as acetic acid, sulfuric acid, phosphoric acid, and hydrochloric acid.

Acid precipitation of the protein in the extract separates the extract into two phases, one phase being the precipitated protein curd, and the other phase being the aqueous extract. The protein curd is separated from the extract to form a protein isolate.

The aqueous extract is cooled to temperatures below 90° F. prior to separating the protein curd from the extract to significantly increase the concentration of isoflavones in the separated protein material. The inventors of the present invention have discovered that separation of the protein curd from the extract under cool or cold conditions can unexpectedly significantly increase the amount of isoflavones captured in the separated protein material. The concentration of isoflavones per unit of recovered protein material, and therefore the total amount of isoflavones in the recovered protein, increases as the temperature at which the separation of the protein curd and extract is effected decreases. Preferably, the protein curd is separated from the extract at a temperature below about 90° F., typically from about 30° F. to about 90° F., more preferably from about 40° F. to about 80° F., and most preferably from about 50° F. to about 70° F.

The aqueous extract containing the protein material may be adjusted to the cool or cold separation temperatures suitable for separating an isoflavone rich protein material at any time after the protein material is extracted from the vegetable protein material and prior to separation of the precipitated protein material from the extract. For example, the temperature of the extract may be adjusted to the cool or cold separation temperatures prior to adjusting the pH of the extract to about the isoelectric point of the protein with an acid, or after acid precipitation of the protein material and prior to separation of the precipitated protein material from the extract.

The temperature of the extract may be adjusted, if necessary, to cool the extract to the desired separation temperature by conventional means prior to separating the protein from the extract. For example, in a large scale commercial process the extract may be passed through a heat exchanger to cool the extract, or in a small scale process the extract may be refrigerated or placed in an ice bath to cool the extract.

The separation may be effected using conventional means for separating solid materials from liquids. Preferably, the isoflavone containing protein material is separated by centrifugation, most preferably utilizing a refrigerated centrifuge. Other separation processes can be utilized as well, such as filtration of the protein material from the extract.

The inventors have also discovered that holding the precipitated protein material at the above cool or cold separation conditions for a period of time prior to separation from the extract can also increase the amount of isoflavones captured in the protein material. The amount of isoflavones captured in the protein material increases with time for a limited time period, typically up to about 1 hour, when the precipitated protein material is held at cool or cold temperatures prior to being separated from the extract at the cool or cold temperatures. Preferably the precipitated protein material is held in the extract prior to separation for at least 30 minutes, and more preferably for about 1 hour, at the cool or cold temperatures at which the protein material is to be separated from the extract.

The yield of the protein material separated at temperatures below about 90° F. can unexpectedly be maintained at a level substantially equivalent to yields of protein material separated according to a conventional procedure by use of the substantially neutral aqueous extractant to extract the protein material and isoflavones, as described above. The protein material extracted by a substantially neutral aqueous extractant and subsequently precipitated packs well at cool or cold temperatures below 90° F. and can be easily separated from the extract. Unlike protein material conventionally extracted with a moderately strong or strongly alkaline extractant, the protein material extracted by a substantially neutral aqueous extractant does not become fluffy at these temperatures. The inventors believe that extracting the protein with a moderately strong or strongly alkaline extractant causes the protein to unfold to a greater extent than when extracted with a substantially neutral extractant due to charge repulsion in the protein induced by the alkaline conditions, which leads to a more fluffy protein precipitate at cool or cold temperatures. The present invention is not to be limited, however, by this proposed mechanism.

The separated isoflavone rich protein material may be dewatered to form an isoflavone rich protein isolate, or alternatively, the separated isoflavone rich protein material may be washed with water and then dewatered to form an isoflavone rich protein isolate. Preferably, washing of the precipitated protein material is avoided entirely to avoid washing the isoflavones from the protein. If the separated protein material is washed, it is preferred to minimize the extent of washing to substantially reduce removal of the isoflavones from the protein. Avoiding or minimizing the washing of the separated protein material can more than double the recovery of isoflavones in the protein compared to a protein isolate formed in accordance with a conventional protein isolate forming process in which the protein material is extensively washed after separation from the extract.

If the protein material is washed, the wash is preferably limited to a single wash with a minimum amount of water. Preferably, if the protein material is to be washed, the wash should be a single wash in which the weight of the water wash used is from 2 to 4 times the weight of the initial vegetable starting material. Further, it is preferred that the temperature of the wash water be cool or cold, preferably from about 30° F. to about 90° F., to further minimize the amount of isoflavones removed in the wash.

After separation of the isoflavone rich protein material from the extract, and any washing of the protein material, the protein material may be dewatered in a conventional manner. Preferably the protein material is dewatered by centrifugation or concentration, or a combination thereof. The dewatered protein material can then be dried using conventional drying techniques, preferably spray drying, to form a dry isoflavone rich protein material.

The isoflavone rich protein material formed by the process of the present invention contains at least 1 mg/g of isoflavones. If the isoflavone rich protein material is unwashed, the material preferably contains at least 2.8 mg/g of isoflavones, and more preferably contains at least 4.2 mg/g of isoflavones. If the isoflavone rich protein material is washed, the material preferably contains at least 1.6 mg/g of isoflavones, and more preferably contains at least 3.2 mg/g of isoflavones. In a preferred embodiment, the isoflavone rich protein material contains from about 2 mg/g of isoflavones to about 40 mg/g of isoflavones, and more preferably contains from about 2.5 mg/g of isoflavones to about 30 mg/g of isoflavones.

The isoflavone rich protein material can be incorporated in a variety of foods to provide the nutritional benefits of the protein and the health benefits of the isoflavones. For example, the isoflavone rich protein material can be used in the following foods: meats, particularly emulsified meats and ground meats; beverages, such as nutritional beverages, sports beverages, protein fortified beverages, juices, milk, milk alternatives, and weight loss beverages; cheeses, such as hard and soft cheeses, cream cheese, and cottage cheese; frozen desserts, such as ice cream, ice milk, low fat frozen desserts, and non-dairy frozen desserts; yogurts; soups; puddings; bakery products; salad dressings; and dips and spreads such as mayonnaise and chip dips. The foods listed above in which the isoflavone rich protein material may be utilized are given as examples, and are not intended to be an exhaustive list of the foods in which the isoflavone rich protein material may be used. The isoflavone rich protein material may be incorporated into any particular food in which protein materials are conventionally incorporated in accordance with conventional processes for incorporating a protein material into the particular food type.

The following non-limiting formulations illustrate dietary supplements that may be formed using an isoflavone rich soy protein material formed in accordance with the process of the present invention. The isoflavone rich soy protein material in the following formulations typically contains between about 1 to about 25 milligrams of the isoflavone compounds of Formulas 1 and 2 above per gram of soy protein.

FORMULATIONS

Formulation 1

Ready to drink beverage

A ready to drink beverage may be formed of the following components:

| Ingredient | Percent of composition, by weight |
| --- | --- |
| Water | 80–85 |
| Isoflavone rich isolated soy protein | 10–15 |
| Sucrose | 5–8 |
| Cocoa | 0.1–1 |
| Vitamins/Minerals | 0.1–1 |
| Flavor | 0.1–1 |
| Cellulose gel | 0.1–0.5 |

The ready to drink beverage may be served in 8 ounce servings containing about 20 grams of isolated soy protein including about 20 to about 500 milligrams of the isoflavone compounds.

Formulation 2

Powdered beverage

A powdered beverage may be formed of the following components:

| Ingredients | Percent of composition, by weight |
| --- | --- |
| Isoflavone rich isolated soy protein | 85–90 |
| Sucrose | 8–15 |
| Maltodextrin | 1–5 |
| Vitamins/Minerals | 0.5–2 |
| Aspartame | 0–0.5 |
| Flavor | 0–0.5 |

30 grams of the powdered beverage formulation may be added to water to form a serving containing about 20 grams of isolated soy protein including about 20 to about 500 milligrams of the isoflavone compounds.

Formulation 3

Food bar

A food bar may be formed of the following components:

| Ingredients | Percent of composition, by weight |
| --- | --- |
| Isoflavone rich isolated soy protein | 20–30 |
| Corn syrup | 35–45 |
| Rice syrup solids | 7–14 |
| Glycerin | 1–5 |
| Cocoa | 2–7 |
| Compound coating | 15–25 |

The food bar may be served in 70 gram portions containing about 15 grams of soy protein having about 15 to about 375 milligrams of the isoflavone compounds therein.

Formulation 4

Soy yogurt

A soy yogurt may be formed of the following components:

| Ingredients | Percent of composition, by weight |
| --- | --- |
| Water | 65–75 |
| Isoflavone rich isolated soy protein | 5–15 |
| Sucrose | 3–8 |
| Corn starch | 1–5 |
| Dextrin | 0.3–1 |
| Cellulose gel | 1–3 |
| Culture (yogurt) | 0.01–0.1 |
| Fruit | 10–20 |
| Vitamins/Minerals | 0.05–0.3 |

The soy yogurt may be served in a 170 gram serving containing about 8 grams of soy protein having about 8 to about 200 milligrams of isoflavone compounds therein.

The following examples are provided to illustrate the present invention. In the examples the term "genistin" is defined to include all of the compounds in the genistein family of isoflavones present in soy, specifically, the total amount of genistin, genistein, 6"-OMal genistin, and 6"-OAc genistin. "Daidzin" is defined in the examples to include all of the compounds in the daidzin family of isoflavones present In soy, specifically, the total amount of daidzin, daidzein, 6"-OMal daidzin, and 6"-OAc daidzin. The examples are not to be interpreted as limiting the scope of the invention.

EXAMPLE 1

In order to illustrate the increased levels of isoflavones in protein isolates produced by a process of the present invention, a conventional protein isolate is provided to show recovery of the desired isoflavones in a conventional process. 100 lbs. of defatted soybean flakes are placed in an extraction tank and extracted with 1,000 lbs. of water heated to 90° F. to which sufficient calcium hydroxide is added to adjust the pH to 9.7. This provides a weight ratio of water to flakes of 10:1. The flakes are separated from the extract and reextracted with 600 lbs. of aqueous extract having a pH of 9.7 and a temperature of 90° F. This second extraction step provides a weight ratio of water to flakes of 6:1. The flakes are removed by centrifugation, and the first and second extracts are combined and adjusted to a pH of 4.5 with hydrochloric acid to precipitate a protein curd. The acid precipitated curd is separated from the extract by centrifugation at 135° F., leaving an aqueous whey, and then is washed with water in a weight amount of seven times that of the starting flake material to provide a protein isolate. The protein isolate, whey, spent flakes, and starting material are analyzed for "genistin" and "daidzin" content. The results are shown in Table 1 below as a concentration of isoflavones and also as a percentage recovery of the isoflavones relative to the amount of isoflavones contained in the starting material.

TABLE 1

| Material | Level (mg/g dry basis) | | % Recovery | |
|---|---|---|---|---|
| | Genistin | Daidzin | Genistin | Daidzin |
| Protein Isolate | 0.90 | 0.54 | 23 | 15 |
| Whey | 3.24 | 3.30 | 75 | 83 |
| Starting Material | 1.72 | 1.58 | — | — |

The above example clearly illustrates that in a conventional process the desired isoflavones are mostly concentrated in the whey, which results in low levels of isoflavones in most commercial protein isolates.

EXAMPLE 2

The effect of extracting protein from a vegetable protein material with a neutral pH extractant followed by separation of the protein from the extract at a relatively cool temperature on isoflavone levels in the separated protein is measured, where the separated protein is washed with an amount of water in accordance with conventional processes for producing protein isolates. Defatted soy flakes are extracted with water having a pH of 6.8 and having a temperature of 90° F. for a period of 15 minutes, where the ratio of the extraction water to flakes is 6:1. The flakes are separated from the extractant and are reextracted with a second volume of water having a temperature of 90° F., where the weight ratio of water to flakes is 4:1. The second extractant is separated from insoluble flake materials by centrifugation and is combined with the first extractant to form a combined extract. The pH of the combined extract is adjusted to pH 4.5 with hydrochloric acid to precipitate a protein curd. The resulting slurry of protein curd/extract is cooled to 43° F. The protein curd is then separated from the extract at 45° F., leaving an aqueous whey. The separated protein curd is washed with 45° F. water, where the wash water has a weight of eight times the starting flake material to provide a protein isolate. The protein isolate, whey, and starting material are analyzed for "genistin" and "daidzin" content. The results are set forth in Table 2 below.

TABLE 2

| Material | Level (mg/g dry basis) | | % Recovery | |
|---|---|---|---|---|
| | Genistin | Daidzin | Genistin | Daidzin |
| Protein Isolate | 1.46 | 0.70 | 31 | 22 |
| Whey | 2.07 | 2.07 | 54 | 14 |
| Starting Material | 1.72 | 1.58 | — | — |

As shown by comparison with the isolate in Example 1, the concentration and percent recovery of the desired isoflavones in the neutral extract protein isolate separated from the whey at cool temperatures are substantially increased compared to the isoflavone concentrations and recovery in a protein isolate prepared in accordance with a conventional process.

EXAMPLE 3

The effect of extracting protein from a vegetable protein material with a neutral pH extractant followed by separation of the protein from the extract at a relatively cool temperature on isoflavone levels in the separated protein is measured, where washing of the separated protein curd is avoided. 100 g of defatted soy flakes are extracted with 600 g of water having a pH of 6.8 and having a temperature of 90° F. for 15 minutes. The flakes are separated from the extractant and are reextracted with 400 g of water having a temperature of 90° F. The second extractant is separated from insoluble flake materials by centrifugation and is combined with the first extract. The pH of the combined extracts is adjusted to pH 4.5 with hydrochloric acid to precipitate a protein curd. The resulting slurry of protein curd/extract is cooled to 43° F. and is held at that temperature for 16 hours. The protein curd is then centrifuged at 10,000 rpm and 43° F. to separate the curd from the extract, leaving an aqueous whey. The resulting protein curd is not washed. The protein curd, whey, and starting material are analyzed for "genistin" and "daidzin" content. The results are set forth in Table 3 below.

TABLE 3

| Material | Level (mg/g dry basis) | | % Recovery | |
|---|---|---|---|---|
| | Genistin | Daidzin | Genistin | Daidzin |
| Protein Curd | 5.49 | 5.22 | 60 | 49 |
| Whey | 2.25 | 4.20 | 25 | 40 |
| Starting Material | 4.29 | 4.54 | — | — |

As shown by comparison with the isolate in Example 1, the relative concentration and percent recovery of the desired isoflavones in the unwashed neutral extract protein curd separated from the whey at cool temperatures are greatly increased compared to the isoflavone concentrations and recovery in a protein isolate prepared in accordance with a conventional process.

EXAMPLE 4

The effect of extracting protein from a vegetable protein material with a neutral pH extractant followed by separation of the protein from the extract at a relatively cool temperature on isoflavone levels in the separated protein is measured, where the separated protein curd is washed with a relatively low amount of water. 100 g of defatted soy flakes are extracted with 600 g of water having a pH of 6.8 and having a temperature of 90° F. for 15 minutes. The flakes are separated from the extractant and are reextracted with 600 g of water having a temperature of 90° F. The second extractant is separated from insoluble flake materials by centrifugation and is combined with the first extract. The pH of the combined extracts is adjusted to pH 4.5 with hydrochloric acid to precipitate a protein curd. The resulting slurry of protein curd/extract is cooled to 43° F. and is held at that temperature for 16 hours. Tile protein curd is then centrifuged at 10,000 rpm and 43° F. for 15 minutes to separate the curd from the extract, leaving an aqueous whey. The resulting protein curd is washed with 43° F. water, where the weight ratio of the water wash to the initial flakes is 2:1 (200 g of water). The resulting protein isolate, whey, and starting material are analyzed for "genistin" and "daidzin" content. Tile results are set forth in Table 4 below.

TABLE 4

| Material | Level (mg/g dry basis) | | % Recovery | |
|---|---|---|---|---|
| | Genistin | Daidzin | Genistin | Daidzin |
| Protein Isolate | 5.12 | 4.57 | 54 | 41 |
| Whey | 2.59 | 4.81 | 31 | 49 |
| Starting Material | 4.29 | 4.54 | — | — |

As shown by comparison with the isolate in Example 1, the relative concentration and percent recovery of the desired isoflavones in the low wash neutral extract protein isolate separated from the whey at cool temperatures are substantially increased compared to the isoflavone concentrations and recovery in a protein isolate prepared in accordance with a conventional process.

EXAMPLE 5

The effect of extracting protein from a vegetable material containing protein and isoflavones with an aqueous extractant having a neutral pH on the yield of recovered protein is measured relative to extracting protein from such a vegetable material with an aqueous alkaline extractant. The extraction and separation efficiencies of the neutral extractant and the alkaline extractant are measured and compared at conventional hot separation temperatures and at cool temperatures which are effective for substantially increasing the isoflavone content of the recovered protein material.

1000 lbs. of commerically available defatted soy flakes are extracted with water having a pH of 6.8 and a temperature of 90° F. The extraction is a countercurrent extraction, where a first quantity of water weighing 10,000 lbs. is used to extract the flakes, and a second quantity of water weighing 6000 lbs. is used to reextract the extracted flakes. The first and second quantities of extractant are combined to form an extract containing protein and isoflavones. A sample of the extract is taken, and the protein content of the sample is determined by Kjeldahl analysis. The extract is then separated into three equal portions. The pH of the portions of the extract is adjusted to 4.5 with hydrochloric acid to precipitate the protein in the extract portions. The temperature of the first portion of the extract is adjusted to 135° F., the temperature of the second portion is adjusted to 65° F., and the temperature of the third portion is adjusted to 43° F. The precipitated protein in each portion of the extract is then separated from the liquid phase of each portion of the extract by centrifugation and decantation of the supernatant. The separated protein of each portion is washed with 4000 lbs. of 65° F. water, and then is dried. The recovered protein material of each portion is then weighed to determine the amount of protein recovered by the extraction and separation process.

The same process is conducted on another 1000 lbs. of defatted soy flakes, except that the extractant is an aqueous alkaline (sodium hydroxide) extractant having a pH of 9.7.

The percentage of protein recovered by the extraction and separation of the three portions of the neutral extract and the three portions of the alkaline extract is calculated. The percentage of protein recovered is calculated as the percentage of protein recovered from the intial flake material, and as the percentage of protein recovered from the extract (as measured by the Kjeldahl analysis). The results are shown in Table 5 below.

TABLE 5

| Extract pH/Separation Temp. | % Protein recovered from flake | % Protein recovered from extract |
|---|---|---|
| pH 9.7/135° F. | 70 | 73 |
| pH 6.8/135° F. | 70 | 77 |
| pH 9.7/65° F. | 60 | 63 |
| pH 6.8/65° F. | 70 | 79 |
| pH 9.7/43° F. | 60 | 65 |
| pH 6.8/43° F. | 69 | 75 |

As shown by comparison of the neutral pH extract protein recovery and the alkaline extract protein recovery at 65° F. and 43° F., the amount of protein recovered utilizing a neutral pH extractant at cool or cold separation temperatures is substantially greater than the amount of protein recovered using an alkaline pH extractant under the same conditions, both from the initial flake material and from the protein extract.

It is to be understood that the foregoing are merely preferred embodiments of the invention and that various changes and alterations can be made without departing from the spirit and broader aspects thereof as set forth in the appended claims, which are to be interpreted in accordance with the principles of patent law including the Doctrine of Equivalents.

What is claimed is:

1. A process for producing an isoflavone rich protein material, comprising:

extracting a vegetable material containing protein and at least one isoflavone with an aqueous extractant having a substantially neutral pH and separating said extractant from insoluble vegetable materials to produce an extract containing said isoflavones and said protein;

adjusting the pH of the extract to about the isoelectric point of said protein to precipitate a protein material containing at least one isoflavone; and separating said protein material from said extract at a temperature of about 40° F. to about 80° F. and avoiding washing of said separated protein material.

2. The process set forth in claim 1 wherein said aqueous extractant has a pH of about 6 to about 8.

3. The process set forth in claim 1 wherein said aqueous extractant has a pH of about 6.5 to about 7.5.

4. The process set forth in claim 1 wherein said vegetable material is a soy material.

5. The process set forth in claim 1 wherein said vegetable material contains at least one isoflavone selected from the group consisting of genistein, genistin, 6"-OMal genistin, 6"-OAc genistin, daidzein, daidzin, 6"-OMal daidzin, 6"-OAc daidzin, glycitein, glycitin, 6"-OMal glycitin, formononetin, biochanin A, or a mixture thereof.

6. The process set forth in claim 1 wherein said protein material is separated from said extract at a temperature of about 50° F. to about 70° F.

7. A process for producing an isoflavone rich protein material, comprising:

extracting a vegetable material containing protein and at least one isoflavone with an aqueous extractant having a substantially neutral pH and separating said extractant from insoluble vegetable materials to produce an extract containing said isoflavones and said protein;

adjusting the pH of the extract to about the isoelectric point of said protein to precipitate a protein material containing at least one isoflavone;

separating said protein material from said extract at a temperature below 90° F.; and washing said separated protein material with water.

8. The process set forth in claim 7 wherein the protein material is washed with water in an amount by weight which is less than about four times the weight of said vegetable material.

9. The process set forth in claim 7 wherein the protein material is washed with water in an amount by weight which is less than about two times the weight of said vegetable material.

10. The process set forth in claim 7 wherein the water used to wash said protein material has a temperature of about 50° F. to about 70° F.

11. The process set forth in claim 7 wherein said aqueous extractant has a pH of about 6 to about 8.

12. The process set forth in claim 7 wherein said aqueous extractant has a pH of about 6.5 to about 7.5.

13. The process set forth in claim 7 wherein said vegetable material is a soy material.

14. The process set forth in claim 7 wherein said vegetable material contains at least one isoflavone of the group consisting of genistein, genistin, 6"-OMal genistin, 6"-OAc genistin, daidzein, daidzin, 6"-OMal daidzin, 6"-OAc daidzin, glycitein, glycitin, 6"-OMal glycitin, formononetin, biochanin A, or a mixture thereof.

15. The process set forth in claim 7 wherein said protein material is separated from said extract at a temperature of about 50° F. to about 70° F.

* * * * *